United States Patent
Aubry et al.

(10) Patent No.: US 7,837,623 B2
(45) Date of Patent: Nov. 23, 2010

(54) NON-INVASIVE METHOD OF OBTAINING A PRE-DETERMINED ACOUSTIC WAVE FIELD IN AN ESSENTIALLY UNIFORM MEDIUM WHICH IS CONCEALED BY A BONE BARRIER, IMAGING METHOD AND DEVICE FOR CARRYING OUT SAID METHODS

(75) Inventors: Jean-François Aubry, Bourg la Reine (FR); Mathias Fink, Meudon (FR); Mickaël Tanter, Paris (FR)

(73) Assignee: Super Sonic Imagine, Aix-En-Provence (FR)

( * ) Notice: Subject to any disclaimer, the term of this patent is extended or adjusted under 35 U.S.C. 154(b) by 1643 days.

(21) Appl. No.: 10/526,561

(22) PCT Filed: Aug. 20, 2003

(86) PCT No.: PCT/FR03/02554
§ 371 (c)(1),
(2), (4) Date: Feb. 28, 2005

(87) PCT Pub. No.: WO2004/019784
PCT Pub. Date: Mar. 11, 2004

(65) Prior Publication Data
US 2005/0277824 A1    Dec. 15, 2005

(30) Foreign Application Priority Data
Aug. 28, 2002    (FR) .................................. 02 10682

(51) Int. Cl.
*A61B 8/00* (2006.01)
(52) U.S. Cl. ..................................................... 600/437
(58) Field of Classification Search ......... 600/437–443; 606/130
See application file for complete search history.

(56) References Cited

U.S. PATENT DOCUMENTS
5,010,885 A    4/1991    Fink et al.
(Continued)

FOREIGN PATENT DOCUMENTS
FR    2 815 717    3/2004
(Continued)

OTHER PUBLICATIONS
Hynynen et al., "Trans-skull Ultrasound Therapy; The Feasibility of Using Image-Derived Skull Thickness Imformation to Correct the Phase Distortion", *IEEE Transactions on Ultrasonics, Ferroelectrics, and Frequency Control*, vol. 46 No. 3, pp. 752-754, (May 1999).
(Continued)

*Primary Examiner*—Long V Le
*Assistant Examiner*—Sanjay Cattungal
(74) *Attorney, Agent, or Firm*—Marshall, Gerstein & Borun LLP

(57) ABSTRACT

A non-invasive method of obtaining a target soundwave field in the brain by means of an array of transducers positioned outside the skull, the method comprising a training stage during which, on the basis of a three-dimensional image giving the porosity of the skull at all points, digital simulation is used to determine individual sound signals to be emitted by the transducers in order to obtain the target soundwave field in the brain. After the training stage, the array of transducers is used to locate the position of the array of transducers relative to the skull by echography and to ensure that the array of transducers is accurately positioned.

31 Claims, 3 Drawing Sheets

U.S. PATENT DOCUMENTS

| | | | |
|---|---|---|---|
| 5,276,654 | A | 1/1994 | Mallart et al. |
| 5,855,582 | A | 1/1999 | Gildenberg |
| 6,359,959 | B1 | 3/2002 | Butler et al. |

FOREIGN PATENT DOCUMENTS

| | | |
|---|---|---|
| FR | 2 791 136 | 8/2004 |
| WO | WO-89/08430 | 9/1989 |

OTHER PUBLICATIONS

Pernot, et al., "Experimental Validation of 3D Finite Differences Simulations of Ultrasonic Wave Propagation Through the Skull", Proceeding from an IEEE conference, 4 pages, (Oct. 2001).

French Preliminary Search Report, FR 0210682; report dated May 9, 2003.

International Search Report, PCT/FR 03/02554; report dated Feb. 4, 2004.

NON-INVASIVE METHOD OF OBTAINING A PRE-DETERMINED ACOUSTIC WAVE FIELD IN AN ESSENTIALLY UNIFORM MEDIUM WHICH IS CONCEALED BY A BONE BARRIER, IMAGING METHOD AND DEVICE FOR CARRYING OUT SAID METHODS

FIELD OF THE INVENTION

The present invention relates to non-invasive methods of obtaining a predetermined soundwave field in a substantially homogeneous medium masked by a bone . barrier, to medical imaging methods implementing such methods, and to apparatuses for implementing the methods.

BACKGROUND OF THE INVENTION

More particularly, the invention relates to a non-invasive method of obtaining at least one predetermined target soundwave field in a substantially homogeneous medium that is masked (totally or partially) by a bone barrier, by causing sound signals to be emitted through said bone barrier by at least one array of transducers (comprising one or more transducers, and possibly comprising a plurality of sub-arrays of transducers).

The term "substantially homogeneous medium" is used herein to mean a medium having characteristics that are substantially homogeneous for soundwave propagation. Such a substantially homogeneous medium may be constituted, for example, by the brain, in which case the bone barrier is constituted by the skull. Where appropriate, the substantially homogeneous medium could be constituted by the heart or by the heart-lung system, in which case the bone barrier would be constituted by the rib cage.

It should be observed that the target soundwave field in question could be constituted by a pulsed wave focused on one or more points of the brain, or by a field that is more complex in terms of space and time.

Document WO-A-02/32316 descries an example of such a method, which gives full satisfaction in terms of its results.

SUMMARY OF THE INVENTION

A particular object of the present invention is to further improve that type of method, in particular in order to obtain more accurate focusing of soundwaves.

To this end, according to the invention, a method of the kind in question is characterized in that it comprises:
a training stage comprising at least the following steps:
1a) making a three-dimensional image of the bone barrier, at least in part by using X-rays, thereby obtaining a parameter representative of the porosity of said bone barrier at various points;
1b) from said three-dimensional image, determining three-dimensional maps of at least density, soundwave speed, and soundwave absorption in said bone barrier;
1c) determining a specific position for the array of transducers relative to the bone barrier;
1d) simulating at least one propagation of soundwaves between at least one point of the substantially homogeneous medium and at least some of the transducers of the array of transducers on the basis of a mathematical model of propagation and said three-dimensional maps of density, soundwave speed, and soundwave absorption; and
1e) on the basis of said simulation, calculating individual sound signals to be emitted by at least some of the transducers of said array of transducers in order to obtain said target soundwave field;
and a stage of actually positioning the array of transducers on the brain barrier, this stage comprising the following steps:
2a) initially positioning the array of transducers on the bone barrier approximately in the specific position;
2b) using at least some of the transducers of the array of transducers to perform echography to locate the position of said array of transducers relative to the bone barrier; and
2c) refining the position of the array of transducers relative to said bone barrier as a function of the location determined in step 2b).

By means of these dispositions, individual sound signals are obtained that a practitioner can subsequently use as a function of requirements in order to obtain very accurate focusing of real soundwaves in zones of the substantially homogeneous medium that the practitioner has determined (or more generally, to generate very accurately a desired wave field), e.g. for static or functional medical imaging purposes and/or for the purposes of treatment by hyperthermia.

In preferred implementations of the method of the invention, recourse may optionally also be had to one or more of the following dispositions:
during step 2b), the relative position between said array of transducers and the bone barrier is located by determining an outside shape of at least a portion of the bone barrier by echography using at least a portion of said array of transducers, and comparing said outside shape with said three-dimensional image of the bone barrier;
in step 1a), an initial step is performed during which a locating device is rigidly secured on said bone barrier, said locating device being adapted to absorb X-rays (at least in part);
during step 1a), the three-dimensional image made also gives the position of the locating device on the bone barrier; and
during step 2b), the relative position between the array of transducers and the locating device is identified by echography;
the array of transducers is included in a fluid-filled tank (filled with a liquid, a gel, or the like) having at least one flexible wall, and during the positioning stage, said flexible wall is pressed against the bone barrier;
the substantially homogeneous medium comprises at least a portion of the brain and the bone barrier comprises at least a portion of a skull surrounding the brain;
the soundwaves are at frequencies lying in the range 0.5 megahertz (MHz) to 3 MHz;
step 1e) is followed by a step 1f) during which emission of sound signals by the array of transducers is simulated, said signals being determined from said individual sound signals and serving to obtain a desired soundwave field, propagation of soundwaves generated by said emission is simulated, and it is verified that said propagation satisfies certain predefined criteria (in particular focusing quality, range of temperatures to be reached locally due to heating by the soundwaves, lack of cavitation, etc.);
during step 1d), propagation of soundwaves from at least one point in the substantially homogeneous medium towards at least some transducers of the array of transducers is simulated (in particular by simulating the emission of a soundwave pulse from said point in the substantially homogeneous medium), and received simulated sound signals $R_i(t)$ reaching the locations of said transducers i of the array of transducers are determined, where i is an integer in the range 1 to n, and n is the number of transducers in the array of transducers; and during step 1e), the individual sound signals Ei(t) for emission by each transducer i under consideration are determined as being proportional to a time reversal Ri(−t) of said received simulated sound signals Ri(t) as previously determined in step 1d);

during step 1e), the sound signals Ei(t) to be emitted are determined by the formula:

$$Ei(t)=Gi \cdot Ri(-t)$$

where Gi is a gain factor that differs from one transducer i to another, for compensating dissipation in the bone barrier;

the gain factors Gi corresponding to at least some of the transducers are respectively inversely proportional to the square of an amplitude of the corresponding received simulated sound signals Ri(t);

during step 1d), the simulation is performed by using a virtual three-dimensional map of soundwave absorption, having absorption coefficients −τ at each point of the bone barrier that are opposite to the real absorption coefficients T determined during step 1b); and during step 1e), the individual sound signals Ei(t) to be emitted are determined as being equal to said time reversal Ri(−t);

the array of transducers is included in a fluid-filled tank (filled with a liquid, a gel, or the like) having at least one flexible wall for pressing against the bone barrier, the specific positions of the transducers as determined during step 1c) not being in contact with the bone barrier, and in which:

during step 1d):

propagation of soundwaves from at least one point of the substantially uniform medium towards at least some transducers of the array of transducers is determined, and received simulated sound signals Ri(t) reaching the locations of said transducers i of the array of transducers are determined, where i is an integer in the range 1 to n, and where n is the number of transducers in the array of transducers;

then emission by each transducer i of a sound signal Ri(−t) corresponding to a time reversal of the signal Ri(−t) is simulated, and propagation in said fluid to a virtual transducer i situated in contact with the bone barrier in correspondence with the transducer i is simulated, and received simulated sound signals R'i(t) reaching the location of said virtual transducer i are determined;

then emission by each virtual transducer i of an acoustic signal G'i·R'i(−t) is simulated where R'i(−t) is a time reversal of the signal R'i(t) and where G'i is a coefficient proportional to the square of an amplitude of the signal R'i(t), at least for some of the virtual transducers i;

then propagation in said fluid to the transducer i is simulated and received simulated sound signals R"i(t) reaching the location of said transducer i are determined;

and during step 1e), the individual sound signals Ei(t) to be emitted are determined as being equal to a time reversal R"i(−t) of said received simulated sound signals R"i(t);

during step 1d), the emission of a soundwave pulse by at least some of the transducers i of the array of transducers is simulated and propagation of soundwaves from each transducer i in consideration towards a plurality of reference points r situated in the substantially uniform medium is simulated, where i is an index in the range 1 to n designating a transducer of the array, and where n is a non-zero natural integer designating the number of transducers, r being an integer in the range 1 to m, where m is a non-zero natural integer designating the number of reference points, and simulated impulse responses hri(t) reaching each of said reference points r of the substantially homogeneous medium are determined, step 1e) comprising the following substeps:

1e1) determining a number p of frequency components for each of the simulated impulse responses, having respective frequencies ωk, where k is an index lying in the range 1 to p and designating a frequency component;

1e2) determining p transfer matrices H(ωk)=[Hri(ωk)], i lying in the range 1 to n, and r going from 1 to m, where Hri(ωk) is the value at the frequency ωk of the Fourier transform of the impulse response Hri(t); and 1e3) for each reference point r, n components Ei(ωk,r) are determined such that:

$$F(\omega k,r)=H(\omega k) \cdot E(\omega k,r)$$

where E(ωk,r)=[Ei(ωk,r)] is a vector having n components Ei(ωk,r), F(ωk,r)=[Fl(ωk,r)] is a vector having m components Fl(ωk,r) where l varies in the range 1 to m, these m components Fl(ωk,r) corresponding to generating said predetermined target soundwave field at the frequency ωk at the points r;

during substep 1e3), p matrices H⁻¹(ωk) are calculated at least by inverting the transfer matrices H(ωk), and for each reference point r of the substantially homogeneous medium, the vector E(ωk,r) is calculated using the formula:

$$E(\omega k,r)=H^{31\ 1}(\omega k) \cdot F(\omega k,r); \text{ and}$$

during step 1d), the impulse responses hir(t) between a plurality of reference points r of the substantially homogeneous medium and at least some of the transducers i of the array of transducers are determined, where i is an index in the range 1 to n which designates a transducer, and where n is a non-zero natural integer which designates the number of transducers, r being an integer lying in the range 1 to m, m being a non-zero natural integer designating the number of reference points, and during step 1e), it is also determined how to focus at least a portion of the array of transducers in reception on each reference point r in order to make an echographic image.

The invention also provides a method of medical imaging by echography, the method comprising a non-invasive method of obtaining a target soundwave field as defined above, and an imaging stage during which at least one echographic image of the substantially homogeneous medium is made using at least a portion of the array of transducers, using the individual sound signals as determined during the training stage.

Finally, the invention also provides apparatus specially designed to implement a method as defined above, the apparatus comprising at least:

an array of transducers adapted to be positioned outside a bone barrier masking a substantially homogeneous medium;

mapper means for determining three-dimensional maps of at least density, soundwave speed, and soundwave absorption in the bone barrier, on the basis of a three-dimensional image of said bone barrier made by X-rays and giving the porosity of said bone barrier at each point;

simulator means for simulating at least one propagation of soundwaves between at least one point of the substantially homogeneous medium and at least some of the transducers of the array of transducers on the basis of a mathematical model of propagation and on the basis of said three-dimensional maps of density, of soundwave speed, and of soundwave absorption, and as a function of a specific position for the array of transducers relative to the bone barrier;

calculator means for responding to said simulation to calculate individual sound signals to be emitted by at least some of the transducers of said array of transducers in order to obtain a target soundwave field in the substantially homogeneous medium;

locator means for using at least some of the transducers of the array of transducers to locate the position of said array of transducers relative to the bone barrier by echography; and position-refine means for refining an initial position of the array of transducers relative to the bone barrier as a function of the position of the array of transducers as located relative to the bone barrier in such a manner that the position of the array of transducers relative to the bone barrier corresponds to the specific position.

In preferred embodiments of the apparatus, recourse may optionally also be had one or more of the following dispositions:

the means for locating the position of said array of transducers relative to the bone barrier are adapted to determine an outside shape of at least a portion of the bone barrier by echography, using at least a portion of said array of transducers, by comparing said outside shape with said three-dimensional image of said bone barrier;

the imaging apparatus comprises a locating device provided with securing means adapted to secure said locating device rigidly on the bone barrier, said locating device being adapted to absorb X-rays and being visible in the three-dimensional image of said bone barrier, and the means for locating the position of said array of transducers relative to the bone barrier are adapted to locate the position of the array of transducers relative to the locating device by echography;

the array of transducers is included in a fluid-filled tank (filled with a liquid, a gel, or the like) having at least one flexible wall for pressing against the bone barrier; and the array of transducers comprises both a sub-array for imaging and a sub-array for hyperthermia treatment, these two sub-arrays comprising transducers of respective different types.

Other characteristics and advantages of the invention appear from the following description of an embodiment thereof given by way of non-limiting example and with reference to the accompanying drawings.

DETAILED DESCRIPTION

In the various figures, the same references are used to designate elements that are identical or similar.

Figure 1:
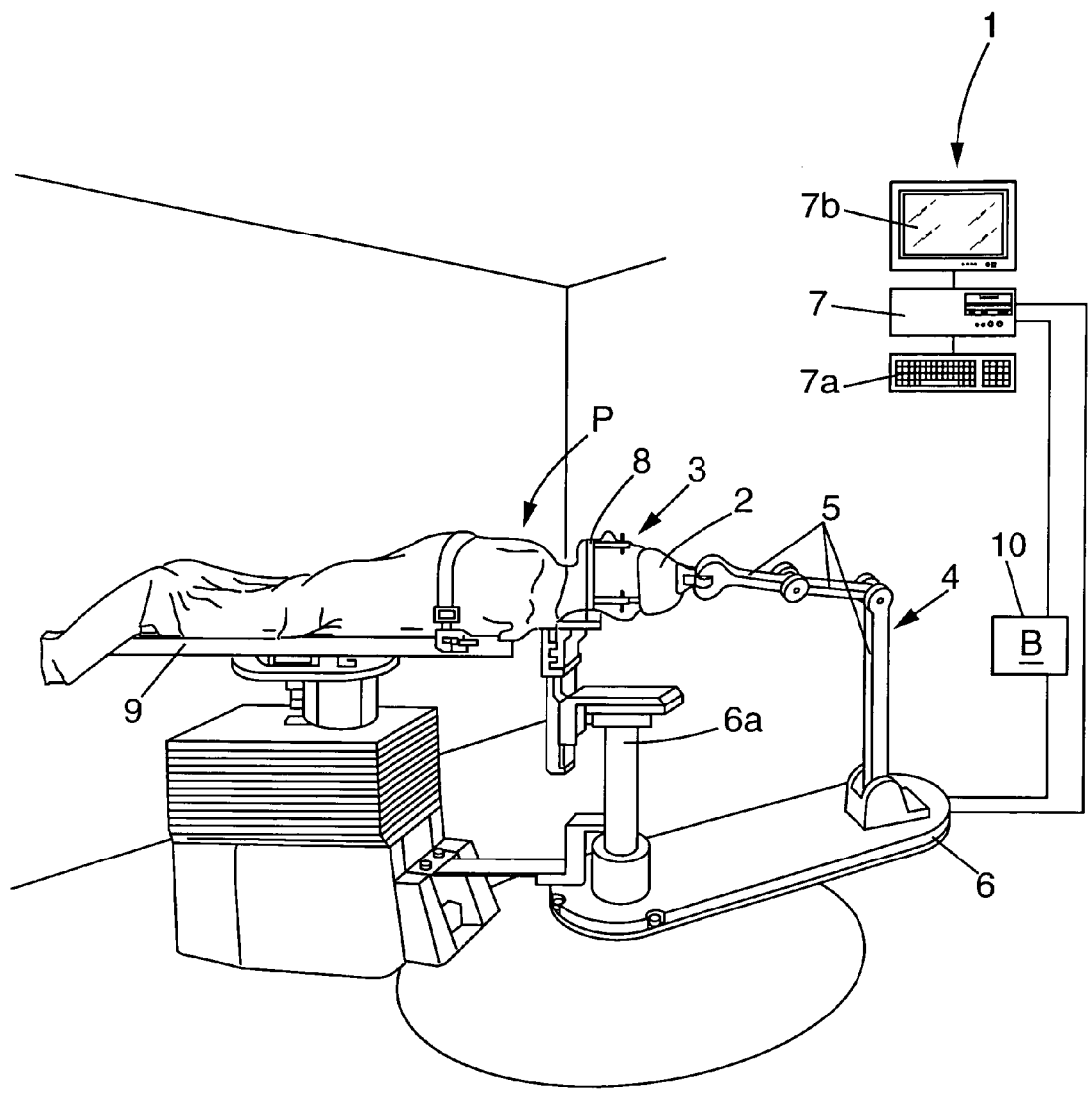
FIG. 1 is a diagrammatic overall view of apparatus for generating ultrasound waves in an embodiment of the invention.

The apparatus 1 for generating soundwaves shown in FIG. 1 is adapted to generate predetermined soundwave fields in a substantially homogeneous medium of the body of a patient P, the substantially homogeneous medium being masked at least in part by a bone barrier.

In the example shown in the drawings, the substantially homogeneous medium is constituted by the patient's brain, and the bone barrier is constituted by the patient's skull.

More generally, the substantially homogeneous medium could be any tissue medium of a human patient or of any other vertebrate, the tissue medium having characteristics for soundwave propagation that are substantially homogeneous. The tissue medium could possibly be constituted by the heart or by the heart and lung system of the patient P, in which case the bone barrier would be constituted by the rib cage.

The apparatus 1 serves to generate ultrasound waves in the brain of the patient P, e.g. at frequencies of the order of 0.5 MHz to 3 MHz, from outside the skull.

This generation of soundwaves can be intended, for example:

to make an echographic image or a series of echographic images of the brain, using static or functional imaging, in particular Doppler imaging for viewing flows of blood, or thermal imaging for viewing heating caused by hyperthermia treatment; and/or to perform hyperthermia treatment, in particular in order to:
   destroy benign or malignant tumors whether single or multiple;
   to coagulate hemorrhages (located by Doppler functional imaging as mentioned above);
   to activate locally medicinal substances that are thermo-activatable; or
   to break locally the blood-brain barrier in order to cause a medicinal substance that has previously been injected intravenously to diffuse locally.

In all cases, it is necessary to be able to generate with as much accuracy as possible one or more predetermined target fields of soundwaves in the brain of patient P, e.g. in order to focus the soundwaves emitted by an array of transducers at one or more points in the brain, or in order to generate wave fields that are more complex.

The array of transducers (not shown in FIG. 1) can be integrated, for example, in a cap 2 that is pressed against the top of the head 3 of the patient P and that is carried by a robotic arm 4 (or by any other positioning system) comprising a plurality of lever arms 5 hinged to one another and carried by a stand 6 that is secured to the floor. In order to position the head 3 of the patient accurately relative to the frame of reference of the robotic arm, it is possible to provide a support 6a that is secured to the stand 6 and on which a rigid stereotaxy frame 8 is secured, which is itself rigidly secured to the skull of the patient P while the patient P is on a table 9.

The robotic arm 6 or other positioning device is advantageously controlled by a microcomputer 7 or the like, provided with an input interface such as a keyboard 7a and with at least one output interface such as a screen 7b. The microcomputer 7 also controls the operation of the array of transducers included in the cap 2, either directly, or preferably via an electronics rack 10(B) for signal processing.

Figure 2:
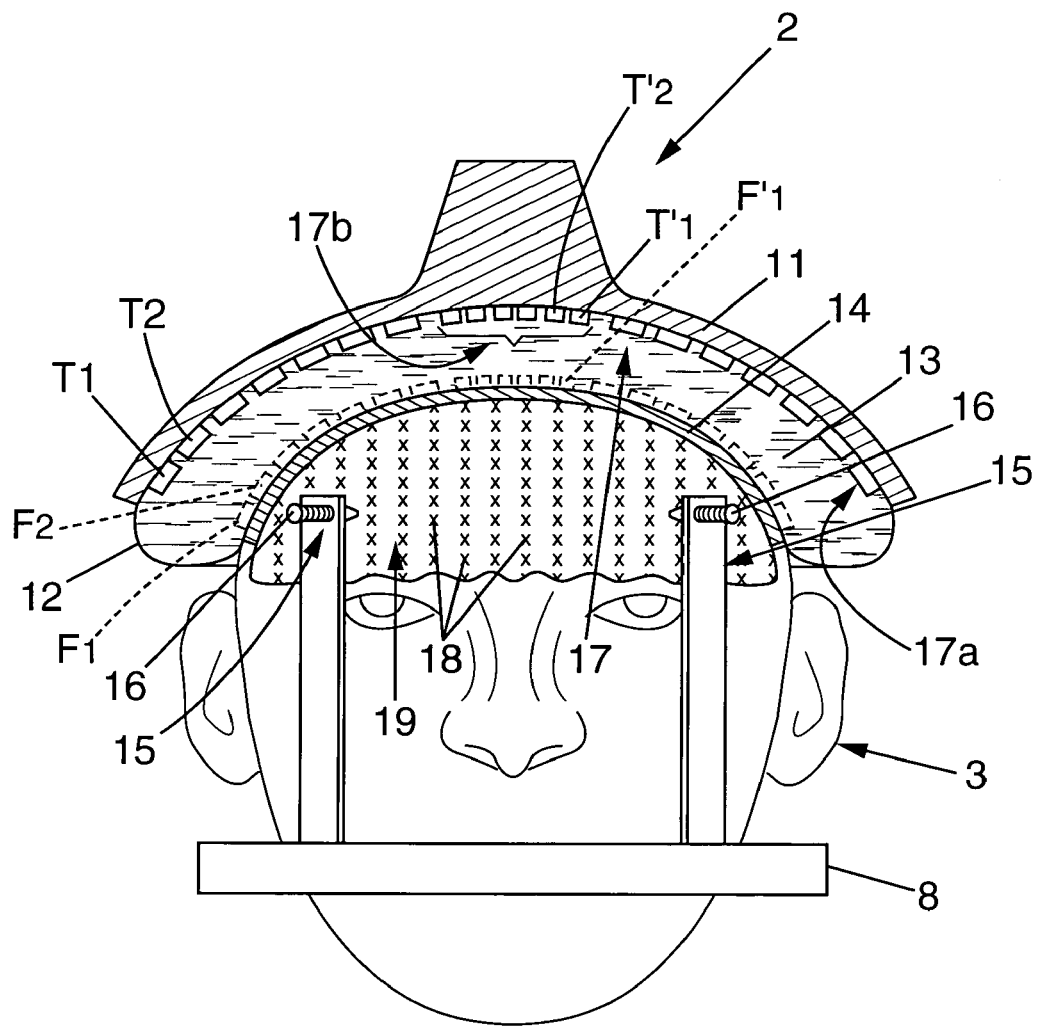
FIG. 2 is a detail view partially in section of a cap forming part of the FIG. 1 apparatus and installed on the head of a patient.

As shown in FIG. 2, the cap 2 may comprise, for example, a rigid cup 11 which co-operates with a flexible wall 12 to define a tank 13 filled with a fluid such as a gel or a liquid, in particular water. The array of transducers 17 is immersed in the fluid on the inside face of the cup 11.

When the cap 2 is placed against the top of the head 3 of the patient by the robotic arm 4, the flexible wall 12 fits closely to the shape of the skull 14 of the patient, possibly covering the top end of rigid holding arms 15 of the stereotaxy frame 8, which arms can be secured to the skull 14 by screws 16.

The array 17 of transducers may comprise a total number n of ultrasound transducers used solely for imaging purposes, or transducers used solely for the purposes of hyperthermia treatment, or indeed ultrasound transducers that are used both for imaging purposes and for hyperthermia treatment purposes.

Optionally, the array 17 of transducers may comprise two sub-arrays:

a hyperthermia treatment sub-array 17a comprising a number n1, not less than 1, e.g. greater than 100, e.g. greater than 200, of transducers T1, T2, T3, . . . , Tn1 that are in acoustic connection with the skull 14 of the patient via the fluid; and an imaging sub-array 17b comprising a number n2, not less than 1 (where n1+n2=n), e.g. greater than 100, or greater than 200, of transducers T'1, T'2, T'3, . . . , T'n2 that are in acoustic connection with the skull 14 of the patient via the fluid and that can, for example, be grouped as a central strip lying substantially in the sagittal plane of the head 3 of the patient.

The transducers of the sub-arrays 17a and 17b are advantageously of two different types. The transducers of the sub-array 17a can thus be larger than the transducers of the sub-array 17b (for example the diameters of these transducers may respectively be about 8 millimeters (mm) and about 1 mm) and they may be adapted to deliver sound at higher power levels.

Figure 3:
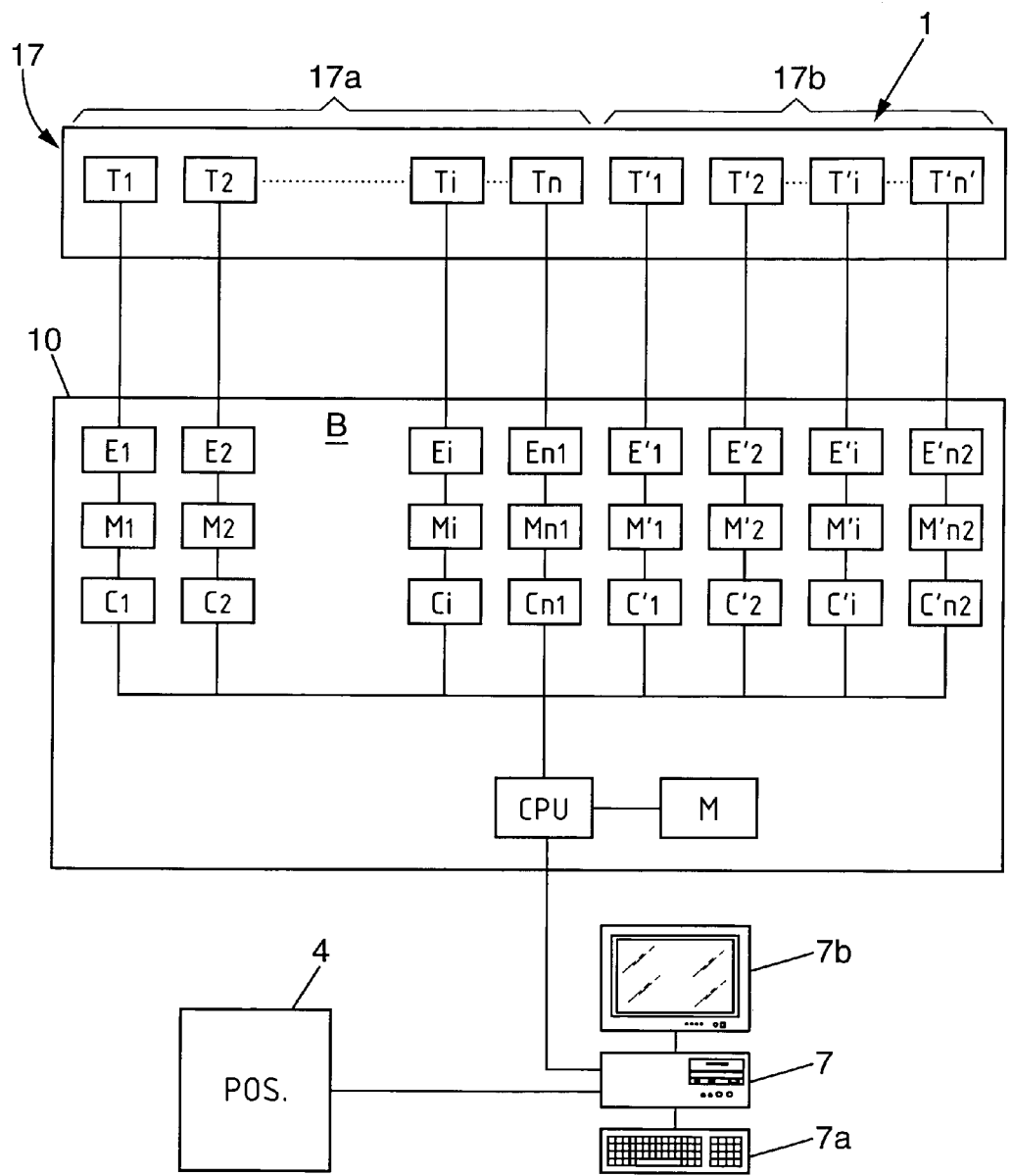
FIG. 3 is a block diagram of the FIG. 1 apparatus.

As shown in FIG. 3, the electronics rack 10 which controls the transducers T1-Tn1, T'1-T'n2 may comprise:

an electronic central unit CPU controlled by the microcomputer 7 which also controls the robotic arm 4 (POS);

at least one central memory M connected to the electronic central unit CPU;

samplers E1, E2, . . . , En1, E'1, E'2, . . . , E'n2 connected respectively to the transducers T1-Tn1, T'1-T'n2;

processors or other electronic central units C1, C2, C3, . . . , Cn1, C'1, C'2, C'3, . . . , C'n2 communicating with the samplers E1-En1, E'1-E'n2; and memories M1, M2, M3, . . . , Mn1, M'1, M'2, M'3, . . . , M'n2 connected respectively to the processors C1-Cn1, C'1-C'n2.

In order to operate the apparatus described above, the stereotaxy frame 8 is initially secured to the outside of the patient's skull 14.

Once the stereotaxy frame 8 is held rigidly to the patient's skull 14, a three-dimensional image of the patient's skull 14 is taken, e.g. by means of a computed tomography scanner (not shown) or a scanner of some other type, serving to obtain a three-dimensional map of the porosity $\Phi$ at each point of the skull 14 (or of a parameter representative of the porosity). This image is advantageously taken with fine resolution, e.g. resolution of about 0.2 mm.

In order to obtain this porosity map, the raw values obtained by the tomography scanner can be converted into Hounsfield units H defined by:

$$H = 1000 \frac{\mu_x - \mu_{water}}{\mu_{bone} - \mu_{water}} \quad (1)$$

where $\mu_x$, $\mu_{bone}$, and $\mu_{water}$ designate respectively the linear photoelectric attenuation coefficients of the tissue being scanned, of bone, and of water, with respect to X-rays.

From the point of view of X-ray absorption, the skull can be considered as being a tissue made of bone having its pores filled with water, and the porosity $\Phi$ of the skull can be considered as being associated with the coefficient $\mu_x$ by the following formula:

$$\mu_x = \Phi \mu_{water} + (1-\Phi) \mu_{bone} \quad (2)$$

The porosity at each point of the skull 14 is thus directly associated with the value H by the following formula:

$$\Phi = 1 - \frac{H}{1000} \quad (3)$$

It is thus possible, from the image given by the scanner, to determine the porosity of the skull 14 or a parameter representative of said porosity (e.g. the density, sometimes given directly by the scanner image with certain types of scanner).

Starting from porosity values $\Phi$ for each point of the skull 14, it is possible to determine a three-dimensional map of density $\rho$, of the speed c of soundwaves, and of the absorption $\tau$ of said soundwaves, at all points of the skull 14.

The density $\rho$ can be calculated using the following formula:

$$\rho = \Phi \times \rho_{water} + (1-\Phi) \times \rho_{bone} \quad (4)$$

where $\rho_{water}$ is the density of water (1000 kilograms per cubic meter (kg·m$^{-3}$)) and $\rho_{bone}$ is the maximum density of cortical bone, which can be estimated as being about 2100 kg·m$^{-3}$.

The speed of soundwaves at the frequencies under consideration can be estimated by the following formula:

$$c = c_{min} + (c_{max} - c_{min}) \times (1-\Phi) \quad (5)$$

where $c_{min}$ corresponds to the speed of soundwaves in water (about 1.5 millimeters per microsecond (mm·µs$^{-1}$)) and $c_{max}$ is the speed of soundwaves in cortical bone (about 2.9 mm·µs$^{-1}$).

The absorption at each point of the skull 14 can be given by the formula:

$$\tau = \tau_{min} + (\tau_{max} - \tau_{min}) \times (\Phi)^\beta \quad (6)$$

where $\tau_{min}$ corresponds to the minimum absorption of soundwaves in cortical bone (e.g. about 0.1 decibels per millimeter (dB·mm$^{-1}$) to 0.5 dB·mm$^{-1}$, and is in particular about 0.2 dB·mm$^{-1}$), where $\tau_{max}$ corresponds to the absorption of soundwaves in cortical bone (e.g. about 0.5 to 15 dB·mm$^{-1}$, and in particular about 8 dB–mm$^{-1}$), and where $\beta$ is a constant coefficient lying in the range 0.3 to 0.7 for example, e.g. being equal to about 0.5.

These various three-dimensional maps of density, speed, and absorption can be calculated in the above-mentioned microcomputer 7, for example, or in any other calculating unit, on the basis of the three-dimensional image obtained by the computed tomography or other scanner. It should be observed that the image obtained by the computed tomography or other scanner also gives the precise position of the stereotaxy frame 8 relative to the skull 14.

On the basis of the differences between the above-mentioned maps, the microcomputer 7, or any other calculating unit, can simulate the propagation of soundwaves through the skull 14 and the brain 19, by considering the brain 19 to be a homogeneous medium, which can be taken to a first approximation as being water concerning its behavior relative to ultrasound waves.

In order to perform this simulation, a user informs the microcomputer of the intended positioning of the array of transducers 17 at the surface of the skull 14 so that the microcomputer can simulate the propagation of ultrasound waves between various points 18 in the brain 19, referred to as reference points, and the locations that are to be occupied by the various transducers T1-Tn1, T'1-T'n2 of the array 17.

This simulation can be performed using a wave equation such as equation (7) below:

$$\left(1 + \tau(\bar{r})\frac{\partial}{\partial t}\right)\left[\rho(\bar{r})\nabla\left(\frac{1}{\rho(\bar{r})}\nabla p(\bar{r}, t)\right)\right] - \frac{1}{c(\bar{r})^2}\frac{\partial^2 p(\bar{r}, t)}{\partial t^2} = S(\bar{r}, t) \quad (7)$$

where $\bar{r}$ designates a position vector for the point in question, p designates pressure, and S designates the sound signals generated by a sound source that might be present at the point under consideration.

The propagation of ultrasound waves in the skull 14 and the brain 19 can be simulated in the microcomputer 7 by finite differences, by putting equation (7) into discrete form. This simulation could also be undertaken by finite elements, or by a pulse diffraction method.

Advantageously, the wave propagation calculation can be lightened by performing the calculation solely by ray tracing in the brain 19 and by finite differences in the skull 14 and in the vicinity of the skull, with the emission of a spherical soundwave being simulated at the interface between the zones corresponding to those two methods of calculation (the spherical wave in question is emitted towards the brain in order to simulate propagation of waves coming from the transducers, and towards the skull in order to simulate propagation of waves coming from the brain).

By means of this simulation, it is possible in a manner that is not invasive, i.e. without necessarily penetrating into the brain 19 of the patient (although such penetration is naturally not excluded, e.g. if it is necessary to undertake a biopsy), to determine individual soundwaves to be emitted by the various transducers T1-Tn of the array 17 in order to obtain a predetermined target field of soundwaves in the brain 19.

By way of example, the target field may be focused on one or more reference points 18 of the brain 19 and/or may be constituted by a wave field that is more complex. In all circumstances, the individual signals to be emitted are determined so as to enable the soundwaves to be accurately focused at various reference points 18 in the brain, thus making it possible subsequently to generate a soundwave field that is more complex by combining the various individual sound signals.

This determination can be undertaken by various methods, and they always involve:

a stage during which the propagation of soundwaves between one or more reference points 18 in the brain and at least some of the transducers T1-Tn1, T'1-T'n2 of the array 17 is simulated (from the brain 19 to the array 17 of transducers and/or from the array 17 to the brain 19): in the present example, these simulations are preferably performed firstly between the reference points 18 and the transducers of the processing sub-array 17a, and secondly between the reference points 18 and the transducers of the imaging sub-array 17b; and a step during which the preceding simulation is used as a basis for calculating the sound signals to be emitted by the transducers under consideration in the array 17 in order to obtain the target soundwave field in the brain 19.

Under all circumstances, determining the individual sound signals to be emitted by the transducers T1-Tn in order to obtain a target soundwave field at one or more points 18 of the brain 19 can be performed in a period lying in the range a few tens of minutes to a few hours depending on the available computer power and depending on the number of reference points 18 taken into consideration. The sound signals as obtained in this way can be used in particular to obtain very accurate soundwave focusing, on focal spots having a diameter of about 1 mm, for example, thus making it possible to obtain excellent echographic imaging precision and also excellent hyperthermia treatment (for example, the precision with which tumors can be treated by radiotherapy is of the order of a few centimeters, i.e. much less accurate, and also gives rise to side effects, unlike treatment by hyperthermia).

It should also be observed that after the step of determining the individual sound signals to be emitted by the transducers T1-Tn1, T'1-T'n2, the method and the apparatus of the invention can make it possible to perform a test of the array 17 of transducers emitting sound signals corresponding to one or more target soundwave fields in the brain 19 in a virtual manner so as to verify by calculation that the propagation of soundwaves in the skull 14 and the brain 19 satisfies certain predefined criteria, in particular concerning focusing quality, obtaining particular temperature ranges by the heating due to the soundwaves, having no cavitation that might lead to lesions, etc.

In order to simulate variation in time and in space of temperature due to heat being supplied by the ultrasound waves, it is possible, for example, to use the following diffusion equation:

$$\rho c_p \frac{\partial T(\bar{r}, t)}{\partial t} - K\Delta T(\bar{r}, t) = \mu \frac{p^2(\bar{r}, t)}{\rho_0(\bar{r})c_0(\bar{r})}$$

where $c_p$ represents the thermal capacity of the medium, K its thermal conductivity, and $\mu$ its coefficient of absorption. The source term of the diffusion equation corresponds to heat being delivered into the medium by the pressure field due to the soundwaves.

Since the three-dimensional distribution of pressure p(r,t) in the medium (skull+brain) has been modeled by digitally simulating wave propagation, this data can be injected into a digital simulation of the above-specified heat diffusion equation by finite differences. This makes it possible prior to treatment to predict how temperature will be distributed during hyperthermia treatment by means of the treatment array 17a, and to check, for example, that temperature does not rise excessively in the bone or in any other sensitive zone that needs to be preserved.

The above-mentioned individual sound signals for obtaining the target soundwave field can be determined in various ways.

In a first method:

soundwave propagation from at least one reference point 18 in the brain to each of the transducers T1-Tn1 or T'1-T'n2 of the sub-array of transducers under consideration is simulated, and the simulated sound signals received Ri(t) reaching the location of each transducer i in the array of transducers belonging the sub-array in question are determined, where i is an integer lying in the range 1 to n, and where n is the number of transducers in the array 17 of transducers; and the individual sound signals to be emitted Ei(t) are determined as being proportional to a time reversal Ri(−t) of said simulated received sound signals Ri(t), as previously determined.

The sound signals to be emitted Ei(t) are thus calculated by the formula:

$Ei(t)=Gi \cdot Ri(-t)$ where Gi is a gain factor which can be:
- identical for all of the transducers (possibly equal to 1); or
- different from one transducer i to another, in order to compensate for dissipation in the skull.

When the gain factors Gi are different from one transducer to another, they may be calculated using the following formula:

$$Gi = \frac{a}{\text{Max}(|Ri(t)|)^2}$$

where a is a real number common to all of the transducers of the array of transducers, and where Max(|Ri(t)|) is a maximum amplitude value in the signal Ri(t). Advantageously, the gain Gi takes this value only for those transducers i that receive a signal of sufficient amplitude (e.g. when Max(|Ri(t)|) is not less than 10% of the greatest value Max(|Ri(t)|) for all of the transducers i in question), and is otherwise equal to 1.

In a second method, the procedure is as above with Gi=1, but soundwave propagation is simulated by using a virtual three-dimensional soundwave absorption map, in which each point of the bone barrier has absorption coefficients −τ that are opposite to the real absorption coefficients τ as determined during step 1b) : dissipation in the medium is thus automatically compensated.

In a third method, the procedure is initially the same as in the above-mentioned first method for calculating the above-mentioned signals Ri(t);

then emission by each transducer i under consideration of a sound signal Ri(−t) corresponding to a time reversal of the signal Ri(t) is simulated together with propagation in the fluid of the tank 13 to a virtual transducer Fi (see FIG. 2) situated at the point of contact with the skull and in correspondence with the transducer i, and simulated received sound signals R'i(t) arriving at a location of said virtual transducer i are determined;

emission by each virtual transducer i of a sound signal G'i·R'i(−t) is then simulated, where R'i(−t) is the time reversal of the signal R'i(t), and where G'i is a coefficient that is inversely proportional to the square of an amplitude of the signal R'i(t), at least for some of the virtual transducers i, for example:

$$Gi = \frac{a}{\text{Max}(|Ri(t)|)^2}$$

where a is a real number common to all of the transducers of the array of transducers, and where Max(|Ri(t)|) is a maximum value of the amplitude of the signal Ri(t); advantageously, the gain Gi takes this value only for those transducers i that receive a signal of sufficient amplitude (e.g. when Max(|Ri(t)|) is not less than 10% of the greatest value for Max(|Ri(t)|) for all of the transducers i under consideration), and is otherwise equal to 1;

then propagation in said fluid to the transducer i is simulated, and received simulated sound signals R"i(t) reaching the location of said transducer i are determined; and the individual sound signals to be emitted Ei(t) are determined as being equal to the time reversal R"i(−t) of said simulated receive sound signals R"i(t).

In a fourth method:

the emission of a soundwave pulse by each transducer i in the array 17 or in one of the sub-arrays 17a, 17b of transducers is simulated, with soundwaves propagating from each transducer i under consideration towards a plurality of reference points r situated in the brain, where i is an index lying in the range 1 to n designating a transducer in the array, and where n is a non-zero natural integer designating the total number of transducers, r being an integer lying in the range 1 to m, and m being a non-zero natural integer designating the number of reference points 18;

the simulated impulse responses hri(t) reaching each of the reference points r in the brain is determined; and the step of calculating the individual sound signals comprises the following substeps:

1e1) determining a number p of frequency components for each of the simulated impulse responses, having respective frequencies ωk, where k is an index lying in the range 1 to p and designating a frequency component;

1e2) determining p transfer matrices H(ωk)=[Hri(ωk)], i lying in the range 1 to n, and r going from 1 to m, where Hri(ωk) is the value at the frequency ωk of the Fourier transform of the impulse response Hri(t); and 1e3) for each reference point r, n components Ei(ωk,r) are determined such that:

$F(\omega k,r)=H(\omega k) \cdot E(\omega k,r)$ where E(ωk,r)=[Ei(ωk,r)] is a vector having n components Ei(ωk,r), F(ωk,r)=[Fl(ωk,r)] is a vector having m components Fl(ωk,r) where l varies in the range 1 to m, these m components Fl(ωk,r) corresponding to generating said predetermined target soundwave field at the frequency ωk at the points r.

During substep 1e3), it is possible for example to calculate p matrices H⁻¹(ωk), at least by inverting the transfer matrices of H(ωk), and for each reference point r (18) of the brain, the vector E(ωk,r) is calculated using the formula:

$E(\omega k,r)=H^{-1}(\omega k) \cdot F(\omega k,r)$

During the above-described training stage, and regardless of which method is used, it is preferable also to determine the impulse responses hir(t) between a plurality of reference points r (18) of the brain and each transducer i of the imaging array 17b (i.e. for soundwaves propagating from the brain to the array 17 of transducers), and it is also determined how to focus the imaging array 17b in reception on each of the reference points 18 in order to make an echographic image.

It is thus possible to use the apparatus 1 for echographic imaging purposes by deconvoluting the sound signals backscattered by the brain 19. This deconvolution can be performed by any known means, e.g. by working in the frequency domain after a Fourier transform on a number p of monochromatic frequency components ωk, by inverting the transfer function H(ωk)=[Hir(ωk)], in which the components Hir(ωk) are the frequency components of the Fourier transform of the impulse responses hir(t) at the frequency ωk. This makes it possible to obtain the signals backscattered by each point of the brain, and in particular the amplitudes of these signals (e.g. the maximum value of each amplitude), thus making it possible to produce an accurate echographic image of the brain 19.

Once the above-mentioned individual sound signals have been determined by simulation, the real array 17 of sound transducers is positioned outside the skull 14 of the patient, in exactly the same position as that which was used during digital simulation.

In order to guarantee that the array 17 of transducers is in the same position as the position used during digital simulation, the cap 2 carrying the array of transducers is initially placed in a position that is approximately correct relative to the skull 14, and then the real position of the cap 2 relative to the skull is located by the imaging sub-array 17*b* performing echographic imaging.

This localization can be performed:

by using echography to locate a relative position between the array of transducers and both portions of the stereotaxy frame 8 that are in contact with the flexible wall 12 of the cap; and/or by directing locating the relative position between the array of transducers and the skull 14, by determining an outside shape for at least one portion of the skull 14 by echography, and then by comparing said outside shape with the three-dimensional image of the skull (this second method can be used on its own, in particular if it is also possible to do without the stereotaxy frame 8).

Starting from this relative position, the microcomputer 7 can move the cap 2 by means of the robotic arm so that its position corresponds exactly to that used for the simulation.

Once the array 17 of transducers has been positioned relative to the skull 14, the practitioner can cause target soundwave fields to be generated at will in the patient's brain 19 as a function of requirements, for example for imaging purposes and/or for hyperthermia treatment purposes.

When the practitioner seeks to perform hyperthermia treatment at one or more zones in the brain, the soundwaves can be focused very accurately on the zone(s) to be treated (where there are a plurality of zones to be treated, this focusing can be performed successively or in parallel).

In all cases, hyperthermia treatment is advantageously performed in successive discontinuous periods so as to avoid heating for too long, which would lead to heat being diffused that might create lesions outside the zones that are to be destroyed. Between periods of hyperthermia treatment, and as explained, it is possible to take successive echographic images of the brain.

The echographic images can advantageous be processed by the microcomputer 7 so as to obtain a temperature map of the brain, in particular by the method known as compound imaging which makes it possible to view the effectiveness of hyperthermia treatment. This method is described in particular by M. Pernot et al. in "Improvement of ultrasound based temperature estimation by compound imaging", Proceedings of the International Symposium on Therapeutic Ultrasound, Seattle 2002, and by Entrekin et al. in Medica Mundi, Vol. 43, September 1999, pp. 35-43, "Real time spatial compound imaging in breast ultrasound: technology and early clinical experience".

The invention claimed is:

1. A non-invasive method of obtaining at least one predetermined target soundwave field in a substantially homogeneous medium masked by a bone barrier by causing sound signals to be emitted by at least one array of transducers through said bone barrier, the method comprising:
a training stage comprising at least the following steps:
1a) making a three-dimensional image of the bone barrier, at least in part by using X-rays, thereby obtaining a parameter representative of the porosity of said bone barrier at various points;
1b) from said three-dimensional image, determining three-dimensional maps of at least density, soundwave speed, and soundwave absorption in said bone barrier;
1c) determining a specific position for the array of transducers relative to the bone barrier;
1d) simulating at least one propagation of soundwaves between at least one point of the substantially homogeneous medium and at least some of the transducers of the array of transducers on the basis of a mathematical model of propagation and said three-dimensional maps of density, soundwave speed, and soundwave absorption; and
1e) on the basis of said simulation, calculating individual sound signals to be emitted by at least some of the transducers of said array of transducers in order to obtain said target soundwave field;
and a stage of actually positioning the array of transducers on the bone barrier, this stage comprising the following steps:
2a) initially positioning the array of transducers on the bone barrier approximately in the specific position;
2b) using at least some of the transducers of the array of transducers to perform echography to locate the position of said array of transducers relative to the bone barrier; and
2c) refining the position of the array of transducers relative to said bone barrier as a function of the location determined in step 2b); and
an imaging stage during which at least one echographic image of the substantially homogenous medium is made using at least a portion of the array of transducers, using the individual sound signals as determined during the training stage.

2. A method according to claim 1, in which, during step 2b), the relative position between said array of transducers and the bone barrier is located by determining an outside shape of at least a portion of the bone barrier by echography using at least a portion of said array of transducers, and comparing said outside shape with said three-dimensional image of the bone barrier.

3. A method according to claim 1, in which:
in step 1a), an initial step is performed during which a locating device is rigidly secured on said bone barrier, said locating device being adapted to absorb X-rays;
during step 1a), the three-dimensional image made also gives the position of the locating device on the bone barrier; and
during step 2b), the relative position between the array of transducers and the locating device is identified by echography.

4. A method according to claim 1, in which the array of transducers is included in a fluid-filled tank having at least one flexible wall, and during the positioning stage, said flexible wall is pressed against the bone barrier.

5. A method according to claim 1, in which, during step 1d), the impulse responses $h_{ir}(t)$ between a plurality of reference points r of the substantially homogeneous medium and at least some of the transducers i of the array of transducers are determined, where i is an index in the range 1 to n which designates a transducer, and where n is a non-zero natural integer which designates the number of transducers, r being an integer lying in the range 1 to m, m being a non-zero natural integer designating the number of reference points, and during step 1e), it is also determined how to focus at least a portion of the array of transducers in reception on each reference point r in order to make an echographic image.

6. (Current)y amended) A non-invasive method of obtaining at least one predetermined target soundwave field in a substantially homogeneous medium comprising at least a portion of a brain masked by a bone barrier comprising at least a portion of a skull surrounding said brain, by causing sound signals to be emitted by at least one array of transducers through said bone barrier, the method comprising:

a training stage comprising at least the following steps:

1a) making a three-dimensional image of the bone barrier, at least in part by using X-rays, thereby obtaining a parameter representative of the porosity of said bone barrier at various points;

1b) from said three-dimensional image, determining three-dimensional maps of at least density, soundwave speed, and soundwave absorption in said bone barrier;

1c) determining a specific position for the array of transducers relative to the bone barrier;

1d) simulating at least one propagation of soundwaves between at least one point of the substantially homogeneous medium and at least some of the transducers of the array of transducers on the basis of a mathematical model of propagation and said three-dimensional maps of density, soundwave speed, and soundwave absorption; and 1e) on the basis of said simulation, calculating individual sound signals to be emitted by at least some of the transducers of said array of transducers in order to obtain said target soundwave field;

and a stage of actually positioning the array of transducers on the bone barrier, this stage comprising the following steps:

2a) initially positioning the array of transducers on the bone barrier approximately in the specific position;

2b) using at least some of the transducers of the array of transducers to perform echography to locate the position of said array of transducers relative to the bone barrier; and 2c) refining the position of the array of transducers relative to said bone barrier as a function of the location determined in step 2b); and an imaging stage during which at least one echographic image of the substantially homogenous medium is made using at least a portion of the array of transducers, using the individual sound signals as determined during the training stage.

7. A method according to claim 6, in which the soundwaves are at frequencies lying in the range 0.5 MHz to 3 MHz.

8. A method according to claim 6, in which step 1e) is followed by a step 1f) during which emission of sound signals by the array of transducers is simulated, said signals being determined from said individual sound signals and serving to obtain a desired soundwave field, propagation of soundwaves generated by said emission is simulated, and verified that said propagation satisfies certain predefined criteria.

9. A method according to claim 8, in which the array of transducers is included in a fluid-filled tank having at least one flexible wall for pressing against the bone barrier, the specific positions of the transducers as determined during step 1c) not being in contact with the bone barrier, and in which:

during step 1d):

propagation of soundwaves from at least one point of the substantially uniform medium towards at least some transducers of the array of transducers is determined, and received simulated sound signals Ri(t) reaching the locations of said transducers i of the array of transducers are determined, where i is an integer in the range 1 to n, and where n is the number of transducers in the array of transducers;

then emission by each transducer i of a sound signal Ri(t) corresponding to a time reversal of the signal Ri(t) is simulated, and propagation in said fluid to a virtual transducer i situated in contact with the bone barrier in correspondence with the transducer i is simulated, and received simulated sound signals R'i(t) reaching the location of said virtual transducer i are determined;

then emission by each virtual transducer i of an acoustic signal G'i.R'i(−t) is simulated where R'i(t) is a time reversal of the signal R'i(t) and where G'i is a reversal coefficient proportional to the square of an amplitude of the signal R'i(t), at least for some of the virtual transducers i;

then propagation in said fluid to the transducer i is simulated and received simulated sound signals R"i(t) reaching the location of said transducer i are determined;

and during step 1e), the individual sound signals Ei(t) to be emitted are determined as being equal to a time reversal R"i(t) of said received simulated sound signals R"i(t).

10. A method according to claim 8, in which during step 1d), the emission of a soundwave pulse by at least some of the transducers i of the array of transducers is simulated and propagation of soundwaves from each transducer i in consideration towards a plurality of reference points r situated in the substantially uniform medium is simulated, where i is an index in the range 1 to n designating a transducer of the array, and where n is a non-zero natural integer designating the number of transducers, r being an integer in the range 1 to m, where m is a non-zero natural integer designating the number of reference points, and simulated impulse responses hri(t) reaching each of said reference points r of the substantially homogeneous medium are determined, step 1e) comprising the following substeps:

1e1) determining a number p of frequency components for each of the simulated impulse responses, having respective frequencies $\omega k$ where k is an index lying in the range 1 to p and designating a frequency component;

1e2) determining p transfer matrices $H(\omega k)=[Hri(\omega k)]$, i lying in the range 1 to n, and r going from 1 to m where $[Hri(\omega k)]$ is the value at the frequency $\omega k$ of the Fourier transform of the impulse response Hri(t); and 1e3) for each reference point r, n components $Ei(\omega k,)$ are determined such that:

$$F(\omega k, r)=H(\omega k)E(\omega k, r)$$

where $E(\omega k, r)=[Ei(\omega k, r)]$ is a vector having n components $Ei(\omega k,r)$, $F(\omega k, r)=[Fl(wk, r)]$ is a vector having m components $Fl(\omega k,r)$ where l varies in the range 1 to m, these m components $Fl(\omega k,r)$ corresponding to generating said predetermined target soundwave field at the frequency $\omega k$ at the points r.

11. A method according to claim 10, in which, during substep 1e3), p matrices $H^{-1}(\omega k)$ are calculated at least by inverting the transfer matrices $H(\omega k,r)$, and for each reference point r of the substantially homogeneous medium, the vector E (ωk,r) is calculated using the formula: E(ωk, r)=H$^{-1}$(ωk).F (ωk, r).

12. A method according to claim 6, in which:

during step 1d), propagation of soundwaves from at least one point in the substantially homogeneous medium towards at least some transducers of the array of transducers is simulated, and received simulated sound signals Ri(t) reaching the locations of said transducers i of the array of transducers are determined, where i is an integer in the range 1 to n, and n is the number of transducers in the array of transducers; and during step 1e), the individual sound signals Ei(t) for emission by each transducer i under consideration are determined as being proportional to a time reversal Ri(t) of said received simulated sound signals Ri(t) as previously determined in step 1d).

13. A method according to claim 12, in which, during step 1e), the sound signals Ei(t) to be emitted are determined by the formula:

Ei(t)=Gi.Ri (−τ)

where Gi is again factor that differs from one transducer i to another, for compensating dissipation in the bone barrier.

14. A method according to claim 13, in which the gain factors Gi corresponding to at least some of the transducers are respectively inversely proportional to the square of an amplitude of the corresponding received simulated sound signals Ri(t).

15. A method according to claim 12, in which:

during step 1d), the simulation is performed by using a virtual three-dimensional map of soundwave absorption, having absorption coefficients −τat each point of the bone barrier that are opposite to the real absorption coefficients −τdetermined during step 1b); and during step 1e), the individual sound signals Ei(t) to be emitted are determined as being equal to said time reversal Ri(t).

16. Apparatus for non-invasively obtaining at least one predetermined target soundwave field in a substantially homogeneous medium comprising at least a portion of a brain masked by a bone barrier comprising at least a portion of a skull surrounding said brain, the apparatus comprising at least:

an array of transducers adapted to be positioned outside a bone barrier masking a substantially homogeneous medium;

mapper means for determining three-dimensional maps of at least density, soundwave speed, and soundwave absorption in the bone barrier, on the basis of a three-dimensional image of said bone barrier made by X-rays and giving the porosity of said bone barrier at each point;

simulator means for simulating at least one propagation of soundwaves between at least one point of the substantially homogeneous medium and at least some of the transducers of the array of transducers on the basis of a mathematical model of propagation and on the basis of said three-dimensional maps of density, of soundwave speed, and of soundwave absorption, and as a function of a specific position for the array of transducers relative to the bone barrier;

calculator means for responding to said simulation to calculate individual sound signals to be emitted by at least some of the transducers of said array of transducers in order to obtain the at least one predetermined target soundwave field in the substantially homogeneous medium;

locator means for using at least some of the transducers of the array of transducers to locate an initial position of said array of transducers relative to the bone barrier by echography, the initial position an approximation of the specific position; and position-refiner means for refining the initial position of the array of transducers relative to the bone barrier as a function of the position of the array of transducers as located relative to the bone barrier in such a manner that the position of the array of transducers relative to the bone barrier corresponds to the specific position.

17. Apparatus according to claim 16, in which the means for locating the position of said array of transducers relative to the bone barrier are adapted to determine an outside shape of at least a portion of the bone barrier by echography, using at least a portion of said array of transducers, by comparing said outside shape with said three-dimensional image of said bone barrier.

18. Apparatus according to claim 16, comprising a locating device provided with securing means adapted to secure said locating device rigidly on the bone barrier, said locating device being adapted to absorb X-rays and being visible in the three-dimensional image of said bone barrier, and the means for locating the position of said array of transducers relative to the bone barrier are adapted to locate the position of the array of transducers relative to the locating device by echography.

19. Apparatus according to claim 16, in which the array of transducers is included in a fluid-filled tank having at least one flexible wall for pressing against the bone barrier.

20. Apparatus according to claim 16, in which the array of transducers comprises both a sub-array for imaging and a sub-array for hyperthermia treatment, these two sub-arrays comprising transducers of respective different types.

21. Apparatus according to claim 16, in which the array of transducers is adapted to emit soundwaves at frequencies lying in the range 0.5 MHz to 3 MHz.

22. Apparatus according to claim 16, further comprising simulator means adapted:

to simulate at least the array of transducers emitting sound signals determined from said individual sound signals and enabling a desired soundwave field to be obtained;

to simulate propagation of soundwaves generated by said emission; and to verify that said propagation satisfies certain predefined criteria.

23. Apparatus according to claim 16, in which:

the simulator means are adapted to simulate soundwave propagation from at least one point of the substantially homogeneous medium towards at least some of the transducers of the array of transducers to determine received simulated sound signals Ri(t) reaching the locations of said transducers i of the array of transducers, i being an integer in the range 1 to n, and n being the number of transducers in the array of transducers; and the calculator means are adapted to determine the individual sound signals Ei(t) to be emitted by each transducer i under consideration as being proportional to a time reversal Ri(t) of said received simulated sound signals Ri(t) as previously determined in step 1d).

24. Apparatus according to claim 23, in which the calculator means are adapted to determine the sound signals Ei(t) to be emitted using the formula:

Ei(t).Ri(t)

where Gi is a gain factor that differs from one transducer i to another, in order to compensate for dissipation in the bone barrier.

25. Apparatus according to claim 24, in which the gain factors Gi corresponding to at least some of the transducers are respectively inversely proportional to the square of an amplitude of the corresponding received simulated sound signals Ri(t).

26. Apparatus according to claim 23, in which:
the simulator means are adapted to perform said simulation of soundwave propagation by using a virtual three-dimensional map of soundwave absorption having at each point of the bone barrier absorption coefficients of −τ opposite to the real absorption coefficient −τ as determined during step 1b); and
the calculator means are adapted to determine the individual sound signals Ei(t) to be emitted as being equal to said time reversal Ri(t).

27. Apparatus according to claim 17, in which the array of transducers is included in a fluid-filled tank having at least one flexible wall for pressing against the bone barrier, the locations provided for the transducers taken into account by the simulator means not being in contact with the bone barrier,
in which apparatus the simulator means are adapted:
to simulate propagation of soundwaves from at least one point of the substantially homogeneous medium towards at least some of the transducers of the array of transducers and to determine the received simulated sound signals Ri(t) reaching the locations of said transducers i of the array of transducers, i being an integer in the range 1 to n, and n being the number of transducers in the array of transducers;
to simulate emission by each transducer i of a soundwave Ri(t) corresponding to a time reversal of the signal Ri(t), and to simulate propagation in said fluid to a virtual transducer i situated in contact with the bone barrier in correspondence with the transducer i, and to determine the received simulated sound signals R'i(t) reaching the location of said virtual transducer i;
to simulate emission by each virtual transducer i of a sound signal G'i.R'(t) where R'i(t) is a time reversal of the signal R'i(t), and where G'i is a reversal coefficient proportional to the square of an amplitude of the signal R'i(t), at least for some of the virtual transducers i; and
to simulate propagation in said fluid to the transducer i, and to determined the received simulated sound signals R"i(t) reaching the location of said transducer i;
and in which the calculator means are adapted to determine the individual sound signals Ei(t) to be emitted as being equal to a time reversal R"i(t) of said received simulated sound signals R"i(t).

28. Apparatus according to claim 16, in which the simulator means are adapted:
to simulate emission of a soundwave pulse by at least some of the transducers i of the array of transducers, and propagation of soundwaves from each transducer i in question towards a plurality of reference points r situated in the substantially homogeneous medium, i being an index in the range 1 to n designating a transducer of the array, and n being a non-zero natural integer designating the number of transducers, r being an integer in the range 1 to m, and m being a non-zero natural integer designating the number of reference points;
to determine simulated impulse responses hri(t) reaching each of said reference points r of the substantially homogeneous medium;
and in which the calculator means are adapted:
to determine a number p of frequency components for each of said simulated impulse responses at respective frequencies ωk, k being an index in the range 1 to p and designating a frequency component
to determine p transfer matrices H(ωk)=[Hri(ωk)], i lying in the range 1 to n and r lying in the range 1 to m, where Hriωk is the value at the frequency ωk of the Fourier transform of the impulse response Hri(t);
and to determine, for each reference point r, n components Ei (ωk,r) such that: F(ωk,r)=H(ωk).E(ωk, r)
where E(ωk,r)=[Ei(ωk,r)] is a vector having n components Ei (ωk,r), F(ωk,r)=[Fl(ωk,r)] is a vector of m components Fl(ωk,r) where l lies in the range 1 to m, these m components Fl(ωk,r) corresponding to generating said predetermined target soundwave field at the frequency ωk at the points r.

29. Apparatus according to claim 28, in which the calculator means are adapted:
to calculate p matrices H⁻¹(ωk) at least by inverting the transfer matrices of H(ωk); and
for each reference point r of the substantially homogeneous medium, to calculate the vector E(ωk,r) by means of the formula:
E(ωk,r)=H⁻¹(ωk).F(ωk,r).

30. Apparatus according to claim 16, in which the simulator means are adapted:
to determine the impulse responses hir(t) between a plurality of reference points r of the substantially homogeneous medium and at least some of the transducers i of the array of transducers, i being an index lying in the range 1to n designating a transducer, and n being a non-zero natural integer designating the number of transducers, r being an integer lying in the range 1to m, and m being a non-zero natural integer designating the number of reference points;
and in which the calculator means are adapted to determine how to focus at least a portion of the array of transducers in reception on each reference point r in order to make an echographic image.

31. Apparatus according to claim 16, further comprising imaging means adapted to make at least one echographic image of the substantially homogeneous medium using at least a portion of the array of transducers, using the individual sound signals determined by the calculator means.

* * * * *